(12) United States Patent
Hartley et al.

(10) Patent No.: US 9,005,268 B2
(45) Date of Patent: Apr. 14, 2015

(54) THORACIC STENT GRAFT (75) Inventors: David Ernest Hartley, Wannanup (AU);
Werner Dieter Ducke, Greenwood (AU); Krasnodar Ivancev, London (GB)

(73) Assignee: Cook Medical Technologies LLC, Bloomington, IN (US)

( * ) Notice: Subject to any disclaimer, the term of this patent is extended or adjusted under 35 U.S.C. 154(b) by 170 days.

(21) Appl. No.: 13/635,579

(22) PCT Filed: Mar. 18, 2011

(86) PCT No.: PCT/US2011/029035
§ 371 (c)(1),
(2), (4) Date: Sep. 17, 2012

(87) PCT Pub. No.: WO2011/116307
PCT Pub. Date: Sep. 22, 2011

(65) Prior Publication Data
US 2013/0013053 A1    Jan. 10, 2013

(30) Foreign Application Priority Data
Mar. 19, 2010 (AU) ................ 2010201067

(51) Int. Cl.
*A61F 2/06* (2013.01)
*A61F 2/07* (2013.01)
*A61F 2/89* (2013.01)

(52) U.S. Cl.
CPC ... *A61F 2/07* (2013.01); *A61F 2/89* (2013.01); *A61F 2002/061* (2013.01); *A61F 2002/065* (2013.01); *A61F 2250/0039* (2013.01); *A61F 2220/0075* (2013.01)

(58) Field of Classification Search
USPC ................... 623/1.35, 1.11, 1.13
See application file for complete search history.

(56) References Cited

U.S. PATENT DOCUMENTS

| 6,811,566 | B1 * | 11/2004 | Penn et al. ........... 623/1.15 |
| 2003/0149472 | A1 | 8/2003 | Pinchuk et al. | |
| 2003/0199967 | A1 * | 10/2003 | Hartley et al. ........... 623/1.13 |
| 2005/0131518 | A1 * | 6/2005 | Hartley et al. ........... 623/1.13 |

(Continued)

FOREIGN PATENT DOCUMENTS

| FR | 2 870 716 A1 | 12/2005 |
| WO | WO 2005/034809 A1 | 4/2005 |

(Continued)

OTHER PUBLICATIONS

International Search Report and Written Opinion for PCT/US2011/029035 dated Jul. 6, 2011, 12 pgs.

*Primary Examiner* — Jacqueline Woznicki
(74) *Attorney, Agent, or Firm* — Brinks Gilson & Lione (57) ABSTRACT

A thoracic arch stent graft (1) has a tubular body of a biocompatible graft material (3) and at least one fenestration (13, 15) in the wall on one side thereof. A combination guide and tubular side arm assembly (20, 22) is mounted into the or each fenestration. The combination guide and tubular side arm assembly comprises a tubular portion (24) and a funnel portion (26) extending from a distal end of the tubular portion. The funnel portion has an angled open end. The tubular portion and the funnel portion are formed from a biocompatible graft material wall and have a lightweight space frame (38 40) formed from a resilient wire and supporting the graft material and defining the combination guide and tubular side arm assembly.

12 Claims, 5 Drawing Sheets

(56) References Cited

U.S. PATENT DOCUMENTS

2007/0219621 A1* 9/2007 Hartley et al. ............... 623/1.13
2012/0029611 A1* 2/2012 Weidman et al. ............ 623/1.13

FOREIGN PATENT DOCUMENTS

WO    WO 2007/028086 A2    3/2007
WO    WO 2010/024867 A1    3/2010

* cited by examiner

Fig 8

THORACIC STENT GRAFT

RELATED APPLICATIONS

The present application is a §371 filing based on PCT Application Serial No. PCT/US2011/029035, filed Mar. 18, 2011 (and published as WO 2011/116307 on Sep. 22, 2011) designating the United States and published in English, which claims priority to Australian Patent Application Serial No. 2010201067, filed Mar. 19, 2010, which foregoing applications are hereby incorporated by reference in their entirety.

TECHNICAL FIELD

This disclosure relates to a medical device and more particularly to a stent graft deployed by endovascular techniques. More particularly it relates to a medical device for treatment of aortic arch disease.

BACKGROUND ART

In recent years endovascular implantable devices have been developed for treatment of aortic aneurysms. These devices are delivered to the treatment site through the vascular system of the patient rather than by open surgery. The devices include a tubular or cylindrical framework or scaffolding of one or more stents to which is secured a tubular shape of graft material such as woven Dacron, polyester polytetrafluoroethylene or the like. The devices are initially reduced to a small diameter, placed into the leading or proximal end of a catheter delivery system. The delivery system is inserted into the vascular system of the patient such as through a femoral incision. The leading end of the delivery system is manoeuvred to the treatment site over a previously positioned guide wire. Through manipulation of a control system that extends to the proximal end of the catheter from the distal end of the system outside the patient the implantable device is then deployed by holding the device as its location and withdrawing a surrounding sheath. The stent graft or implantable device can then be released and self expand or be expanded through the use of a balloon which is introduced with the stent graft introducible device. The stent graft becomes anchored into position to healthy wall tissue in the aorta such after which the delivery system is removed leaving the device in position thereby bypassing an aneurysm in the aorta in a manner that channels all blood flow through the stent graft so that no blood flow enters the aneurysm, such that not only does the aneurysm no longer continue to grow and possibly rupture but the aneurysm actually begins to shrink and commonly disappears entirely.

For treatment of thoracic aortic aneurysms in particular it is necessary to introduce the implantable device high up in the aorta and in a region of the aorta which is curved and where there can be strong blood flow.

In the thoracic aorta there are major branch vessels, the brachiocephalic, the left carotid and the left subclavian and for treatment of an aneurysm in the region of the thoracic arch provision must be made for blood supply to continue to these arteries while an operation is in progress and after completion of the operation. For this purpose fenestrations or side branches are provided into a stent graft in that region. Access is generally obtained to these fenestrations to deploy side arms into the stent graft via the left or right brachial arteries or less commonly via the left or right carotid arteries. Once a guide wire has been introduced towards the thoracic arch via such an artery the fenestration must be accessed and then catheterised. For this reason it is desirable to provide an arrangement where access and subsequent catheterisation is possible even if there is a degree of mis-alignment between the fenestration and the respective branch artery.

The disclosure will be discussed in relation to a stent graft suitable for the thoracic arch of a patient but it is not so limited and may be applicable to any body cavities where access into a prosthetic device such as a stent graft is required from a side branch vessel.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

DISCLOSURE OF THE INVENTION

In one form the disclosure is said to reside in a thoracic arch stent graft comprising a tubular body of a biocompatible graft material at least one aperture in the tubular body on one side thereof, a combination guide and tubular side arm assembly being mounted into the or each aperture, the combination guide and tubular side arm assembly comprising a tubular portion and a funnel portion extending from a distal end of the tubular portion, the funnel portion comprising a frusto-conical body comprising a smaller end and a larger end, the smaller end being connected to the tubular portion and the larger end comprising an angled open end, the tubular portion and the funnel portion comprising a biocompatible graft material wall and a lightweight space frame, the lightweight space frame comprising a resilient wire, the lightweight space frame supporting the combination guide and tubular side arm assembly.

Preferably the space frame comprises a cylindrical portion and a funnel portion, the cylindrical portion comprising first and second circular planar ring portions, the circular planar ring portions being parallel to each other and spaced apart axially and at least two longitudinal struts extending between the first and second circular ring portions and the funnel portion comprising a funnel frame defined by a substantially circular ring portion to define the larger end of the funnel portion and a pair of spaced apart arms extending towards the cylindrical portion.

The cylindrical portion can comprise an assembly of two ring and strut components, each ring and strut component comprising a circular planar ring portion and a strut extending at right angles to the circular planar ring portion from a periphery of the circular ring portion.

Preferably the aperture comprises a periphery and the tubular side branch is mounted into the aperture by being stitched to the tubular body around the periphery of the aperture to seal therein.

Preferably the stitching by which the tubular side branch is mounted and sealed into the aperture extends circumferentially and diagonally in a semi-helical manner from the proximal end of the tubular side branch to the distal end of the tubular side branch such that the tubular side branch extends from the tubular body at an angle thereto with the funnel portion opening distally.

In an alternative arrangement the or each aperture may be in the tapered portion of the tubular body and wherein the stitching by which the tubular side branch is mounted into the fenestration extends circumferentially and diagonally from the proximal end of the tubular side branch to the distal end the angle between the tubular side branch and the wall of the tubular body in that region may be such that the tubular side branch extends substantially parallel to the tubular body as a whole with the funnel portion opening distally.

Preferably the space frame comprises a cylindrical portion and a funnel portion, the cylindrical portion comprising first and second circular ring portions defining planes parallel to each other spaced apart axially and at least two longitudinal struts extending between the first and second circular ring portions and the funnel portion comprising a funnel frame defined by a substantially circular ring portion and a pair of spaced apart arms extending towards the cylindrical portion.

In one embodiment the cylindrical portion comprises an assembly of two ring and strut components, each ring and strut component comprising a circular ring portion defining a plane of the circular ring portion and a strut extending at right angles to the plane of the circular ring portion from a periphery of the circular ring portion. Each of the two ring and strut components and the funnel frame can comprise a single length of the resilient wire.

Preferably there are two apertures in the graft wall on one side thereof and the two apertures being spaced longitudinally apart and one of the combination guide and tubular side arm assemblies being mounted into each aperture. The two apertures can also be spaced circumferentially apart to more closely follow the natural position of the arteries extending from the thoracic arch.

In an alternative form the disclosure comprises a thoracic arch stent graft comprising a tubular body of a biocompatible graft material and two apertures in the tubular body on one side thereof, the two apertures in the tubular body on one side thereof and the two apertures being spaced longitudinally and transversely apart, a combination guide and tubular side arm assembly being mounted into each aperture, the combination guide and tubular side arm assembly comprising a tubular portion and a funnel portion extending from a distal end of the tubular portion, the funnel portion comprising a frusto-conical body comprising a smaller end and a larger end, the smaller end being connected to the tubular portion and the larger end comprising an angled open end, the tubular portion and the funnel portion comprising a biocompatible graft material wall and a lightweight space frame, the lightweight space frame comprising a resilient wire and the lightweight space frame supporting the combination guide and tubular side arm assembly, the space frame comprising a cylindrical portion and a funnel portion, the cylindrical portion comprising first and second circular ring portions defining planes parallel to each other spaced apart axially and at least two longitudinal struts extending between the first and second circular ring portions and the funnel portion comprising a funnel frame defined by a substantially circular ring portion to define the larger end of the funnel portion and a pair of spaced apart arms extending towards the cylindrical portion.

In an alternative form the disclosure comprises a combination guide and tubular side arm assembly, the combination guide and tubular side arm assembly being for installing into a stent graft to provide an accessible side arm, the combination guide and tubular side arm assembly comprising a tubular portion and a funnel portion extending from a first end of the tubular portion, the funnel portion comprising a frusto-conical body comprising a smaller end and a larger end, the smaller end being connected to the tubular portion and the larger end comprising an angled open end, the tubular portion and the funnel portion comprising a biocompatible graft material wall and a lightweight space frame, the lightweight space frame comprising a resilient wire, the lightweight space frame supporting the graft material.

Preferably the space frame comprises a cylindrical portion and a funnel portion, the cylindrical portion comprising first and second circular planar ring portions, the circular planar ring portions being parallel to each other and spaced apart axially and at least two longitudinal struts extending between the first and second circular ring portions and the funnel portion comprising a funnel frame defined by a substantially circular ring portion to define the larger end of the funnel portion and a pair of spaced apart arms extending towards the cylindrical portion.

Preferably the cylindrical portion comprises an assembly of two ring and strut components, each ring and strut component comprising a circular planar ring portion and a strut extending at right angles to the circular planar ring portion from a periphery of the circular ring portion. Each of the two ring and strut components and the funnel frame can comprise a single length of the resilient wire.

It will be seen that that by this disclosure there is provided a funnel guide arrangement which will assist with catheterisation of a fenestration in a stent graft from a branch vessel. In addition the funnel guide assembly is a relatively lightweight construction with the supporting space frame so that after fulfilling its guiding function the funnel can relatively easily collapse so that it does not block the aorta any more than necessary with a prosthetic device.

BRIEF DESCRIPTION OF THE DRAWINGS

This then generally describes the disclosure but to assist with understanding reference will now be made to the accompanying drawings which show preferred embodiments of the disclosure.

In the drawings.

BEST MODE FOR CARRYING OUT THE INVENTION

Figure 8:
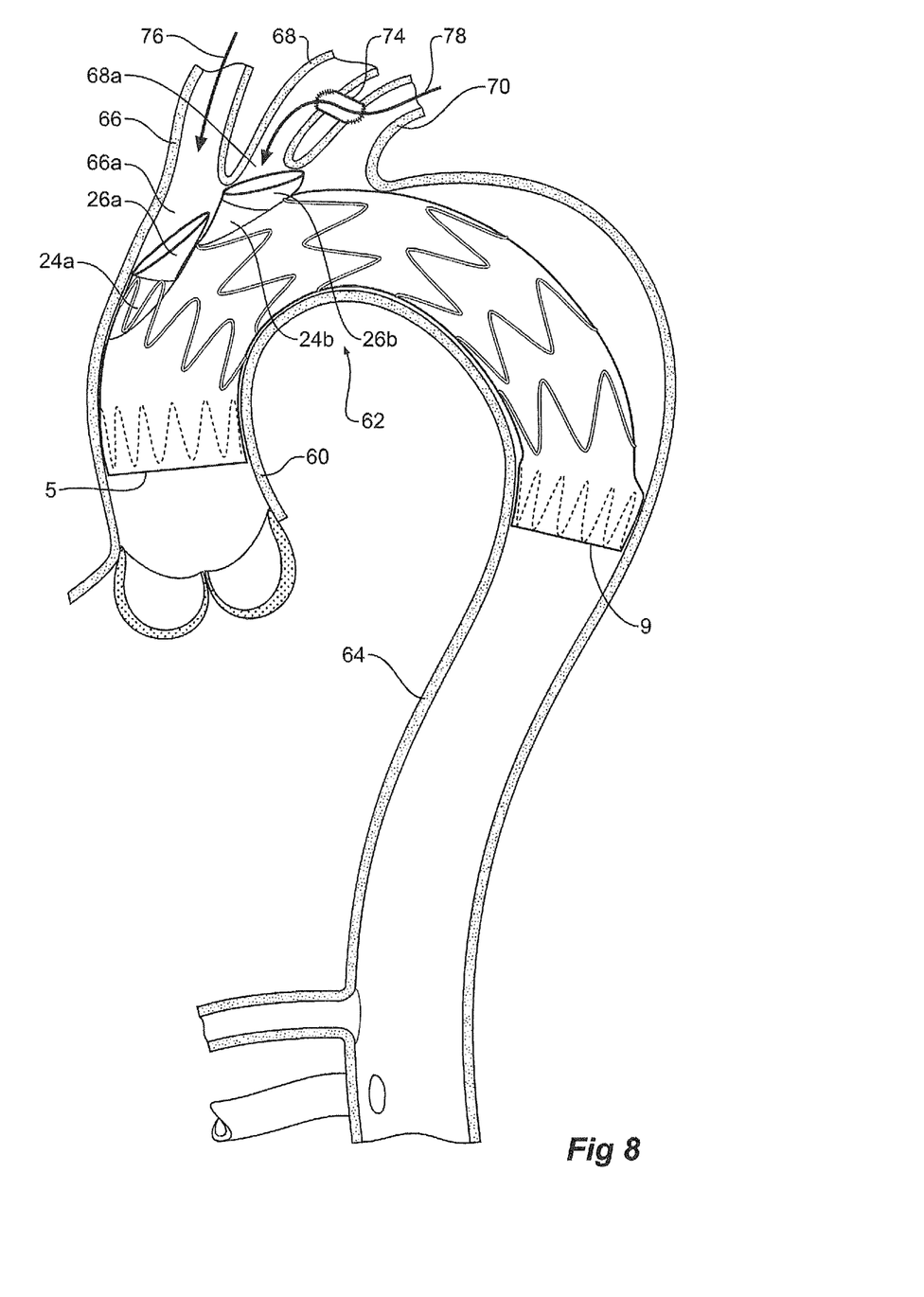
FIG. 8 shows a schematic view of a portion of the human aorta showing how the stent graft as depicted in FIG. 1 can be deployed into the aorta.

In FIGS. 1 to 5 of the drawings a first embodiment of the stent graft of the present disclosure is shown. The stent graft 1 comprises a tubular body 3 of a biocompatible graft material. In this embodiment the stent graft is intended for deployment into the thoracic arch of a patient. The full length of the stent graft may be from 10 to 20 cm long. The tubular body 3 is supported by a plurality of self expanding stents 11. The stent graft has a proximal fenestration 13 and a distal fenestration 15 on one side of the tubular body and towards a proximal end 5. The proximal fenestration 13 is for subsequent placement of a side branch stent graft extending from the innominate or brachiocephalic artery and the distal fenestration 15 is intended for subsequent placement of a side branch stent graft extending from, usually, the left subclavian artery. In many situations a physician will provide a crossover graft between the left carotid artery and the left subclavian artery so that the distal fenestration 15 will serve the left carotid artery and the left subclavian artery as is shown in FIG. 8.

The tubular body is shown in a substantially cylindrical configuration but the placement of the stents 11 allows a longitudinally curved configuration to accord with the form of the thoracic arch of a patient when the stent graft is deployed therein. This can be achieved by placement of the stents so that the points or bends of adjacent stents do not coincide particularly on the underside of the tubular body where the most curvature is required. The tubular body is adapted for placement into the thoracic arch of a patient with the proximal end 5 extending down the ascending aorta, the arched portion 7 in the thoracic arch and the distal end 9 in the descending aorta. (See also FIG. 8).

Catheterization of each the proximal fenestration 13 and the distal fenestration 15 from the brachiocephalic artery and the left subclavian artery, respectively, can be difficult due the variations in relative position of each of these arteries both along the length of the thoracic arch and circumferentially around the thoracic arch and because of compound curvature of the thoracic arch. It is preferable to place the stent graft into the thoracic arch so that the proximal fenestration 13 and the distal fenestration 15 are slightly proximal of the expected positions of the arteries and then to have the funnel assemblies of the present invention, as discussed below in detail, assist in providing the guidance and the space needed for catheterization.

Figure 3:
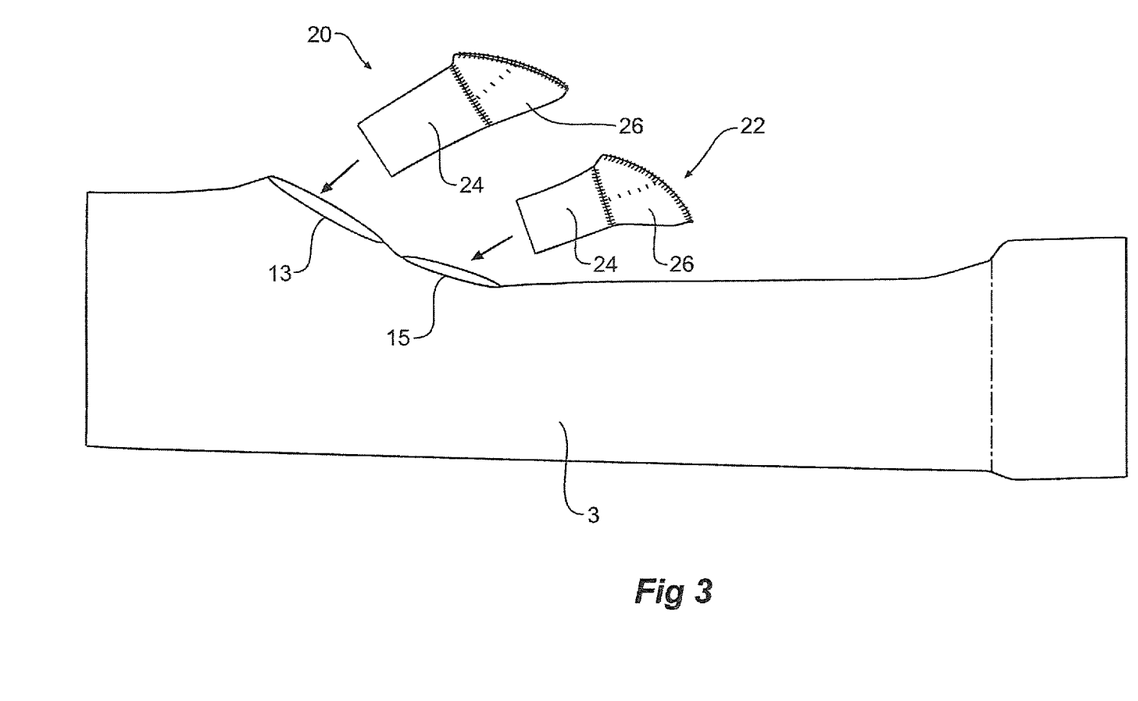
FIG. 3 shows a schematic view showing the assembly of the embodiment of FIG. 1.
Figure 4:
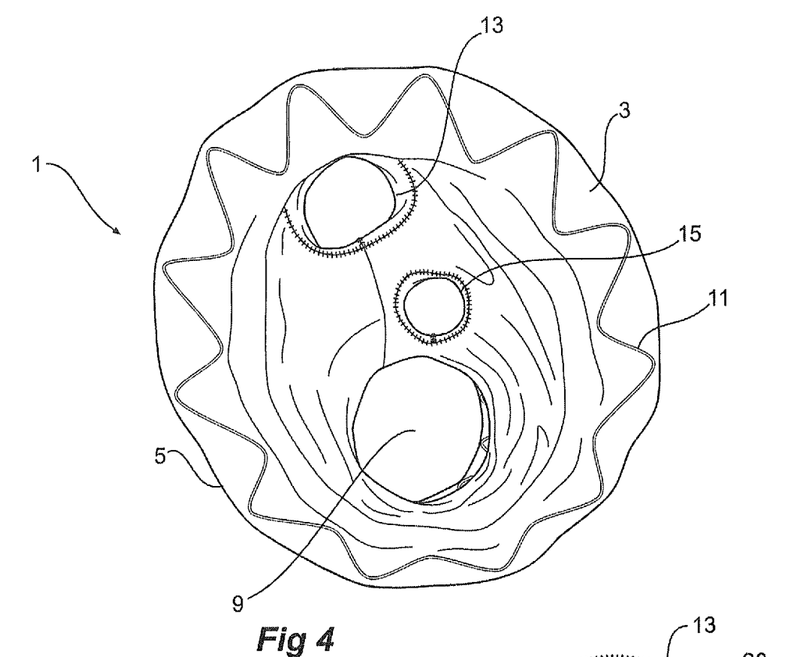
FIG. 4 shows the embodiment of FIG. 1 from the proximal end.

Each of the fenestrations 13 and 15 has mounted into it a combination guide and tubular side arm assembly by stitching (although other forms of mounting such as by biocompatible adhesives are within the scope of the disclosure). FIG. 3 shows the proximal combination guide and tubular side arm assembly 20 and the distal combination guide and tubular side arm assembly 22 adjacent to the fenestrations 13 and 15 respectively before mounting them therein.

Figures 6, 7A, 7B, 7C, 7D:
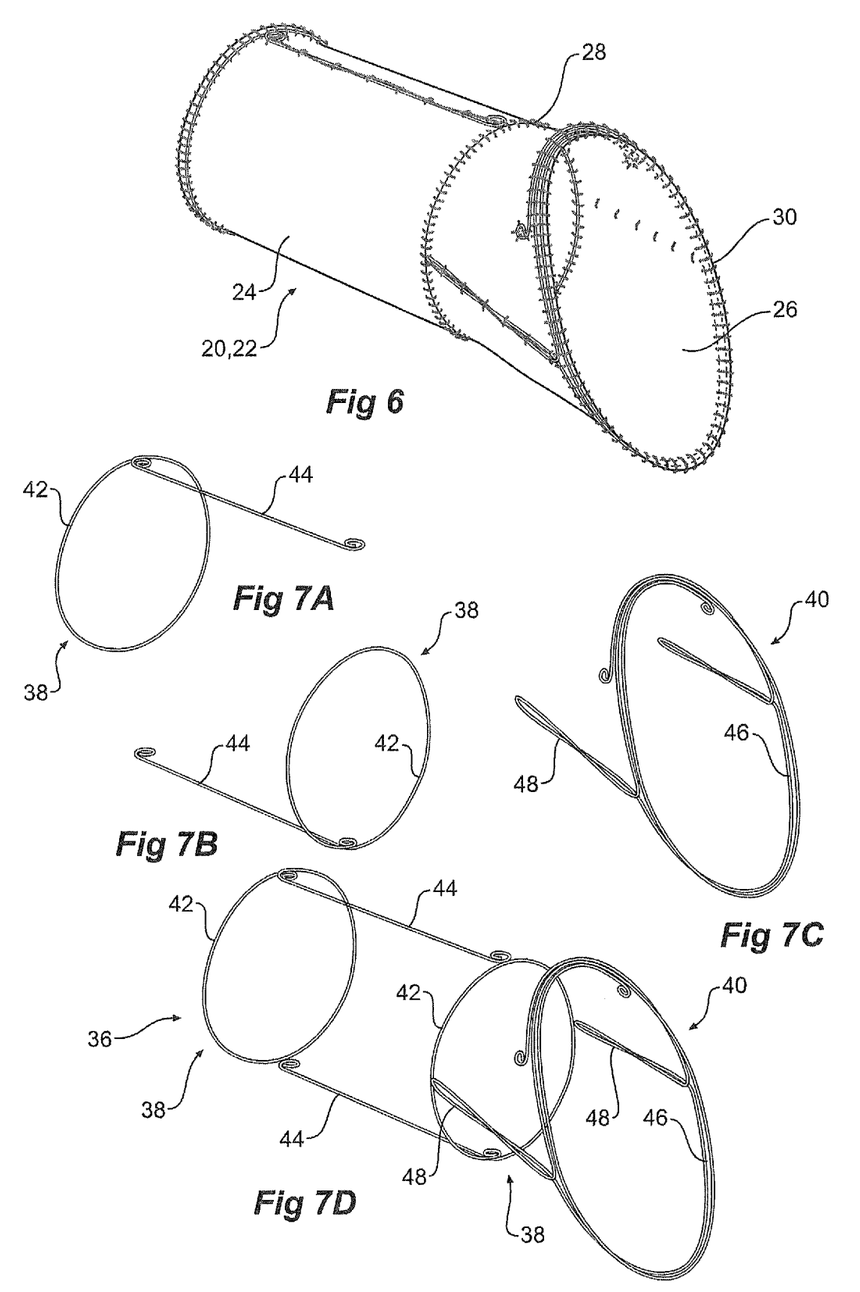
FIG. 6 shows detail of a combination guide and tubular side arm assembly of one embodiment of the disclosure.
FIGS. 7A to 7D show the various portion of the space frame arrangement by which the combination guide and tubular side arm assembly is supported.

Each of the combination guide and tubular side arm assemblies 20, 22 as can be best seen in FIG. 6 comprise a tubular portion 24 and a funnel portion 26 extending from a distal end 28 of the tubular portion 24. Both the tubular portion 24 and the funnel portion 26 are formed from a biocompatible graft material such as Dacron. The funnel portion 26 comprises a frusto-conical body comprising a smaller end and a larger end, the smaller end being connected to the tubular portion 24 and the larger end comprising an angled open end 30. Hence there is a tapering frusto-conical wall extending back towards the distal end 28 of the tubular portion 24. The tubular portion 24 and the funnel portion 26 define the biocompatible graft material wall and have a lightweight space frame 36 formed from a resilient wire and supporting and defining the combination guide and tubular side arm assembly 20, 22. The lightweight space frame 36 can be best seen in FIG. 7D and the components of the lightweight space frame 36 can be seen in FIGS. 7A to 7C.

In this embodiment the components of the lightweight space frame 36 are an assembly of two ring and strut components 38 and a funnel portion 40. Each ring and strut component 38 comprises a circular ring portion 42 defining a plane of the circular ring portion and a strut 44 extending at right angles to the plane of the circular ring portion from a periphery of the circular ring portion as shown in FIGS. 7A and 7B. The funnel portion 40 comprises a funnel frame defined by a circular ring portion 46 and a pair of spaced apart arms 48 on each side of the circular ring portion 46 and extending back towards the cylindrical portions 38.

Each of the two ring and strut components 38 and a funnel portion 40 are formed from a single length of a rigid but resilient wire such as a nitinol which is a nickel titanium alloy wire. At each end of each piece of wire a loop is formed to ensure that a sharp end which could puncture a vessel wall is not present.

Once the components of the lightweight space frame 36 are individually formed they have stitched to them portions of biocompatible graft material to form separately the tubular portion 24 and the funnel portion 26 and then these are joined together by stitching or the like.

The two combination guide and tubular side arm assemblies 20, 22 are then mounted into the fenestrations 13 and 15 respectively with stitching or other fastening 50 extending diagonally on the tubular portion 24 from one end of the tubular portion to the other. The stitching 50 by which the tubular side branch 20, 22 is mounted and sealed into the aperture or fenestration 13, 15 extends circumferentially and diagonally from the proximal end of the tubular side branch to the distal end of the tubular side branch such that the tubular side branch extends from the tubular body at an angle thereto.

This in effect makes the tubular portion 24 a low profile side arm with half of the tubular portion within the stent graft and the other half outside the stent graft. The disposition of the tubular portions to define a low profile side arm can be best seen in the longitudinal cross section shown in FIG. 2. The tubular portions 24 in the form of a low profile side arm with half of the tubular portion within the stent graft and extending proximally and the other half outside the stent graft and extending distally act as sockets for subsequently placed side arms from the branch vessels.

Figure 5:
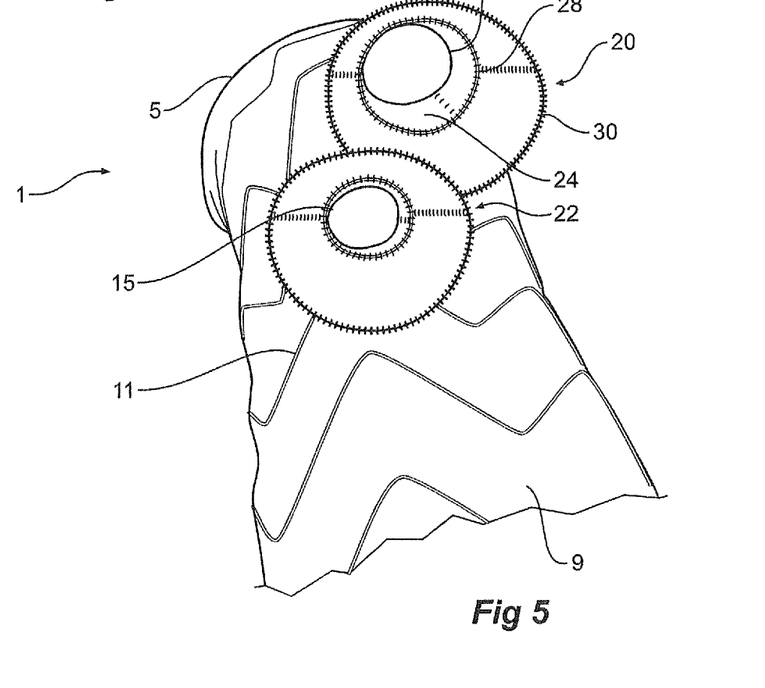
FIG. 5 shows the embodiment of FIG. 1 from towards the distal end and in particular showing the funnel openings.

FIG. 5 particularly shows a view from towards the distal end of the stent graft 3 and it can be seen that the funnel openings provide a useful guide for the catheterisation of the fenestrations 13 and 15 respectively. The frusto conical shape of the funnel portions 26 will assist in guiding a guide wire into the fenestrations.

Figure 1:
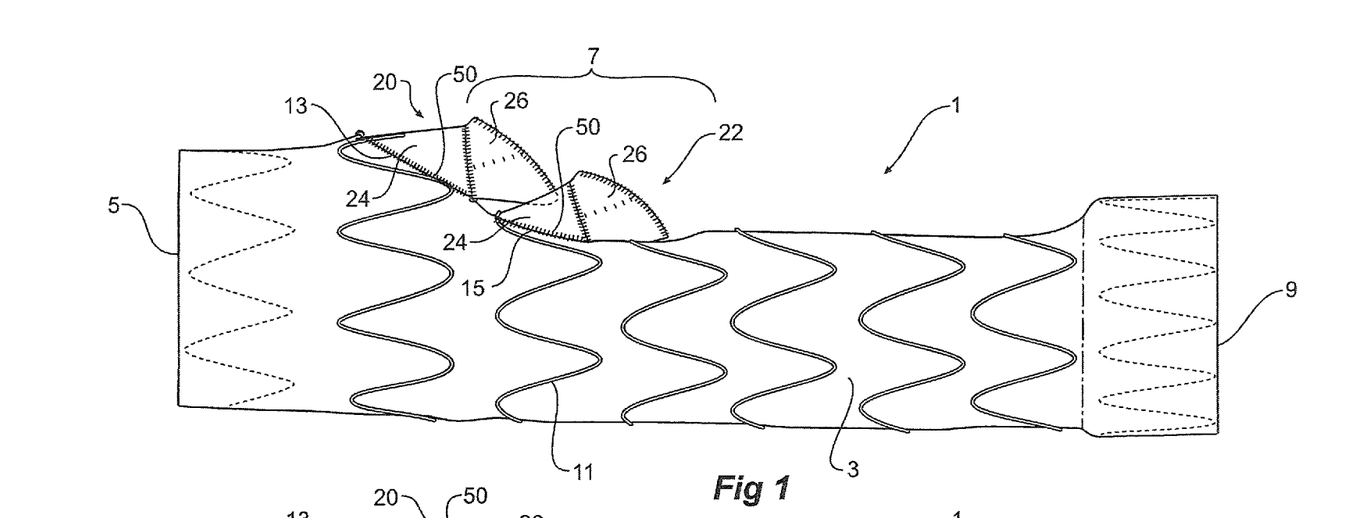
FIG. 1 shows a stent graft incorporating a first embodiment of the present disclosure.
Figure 2:
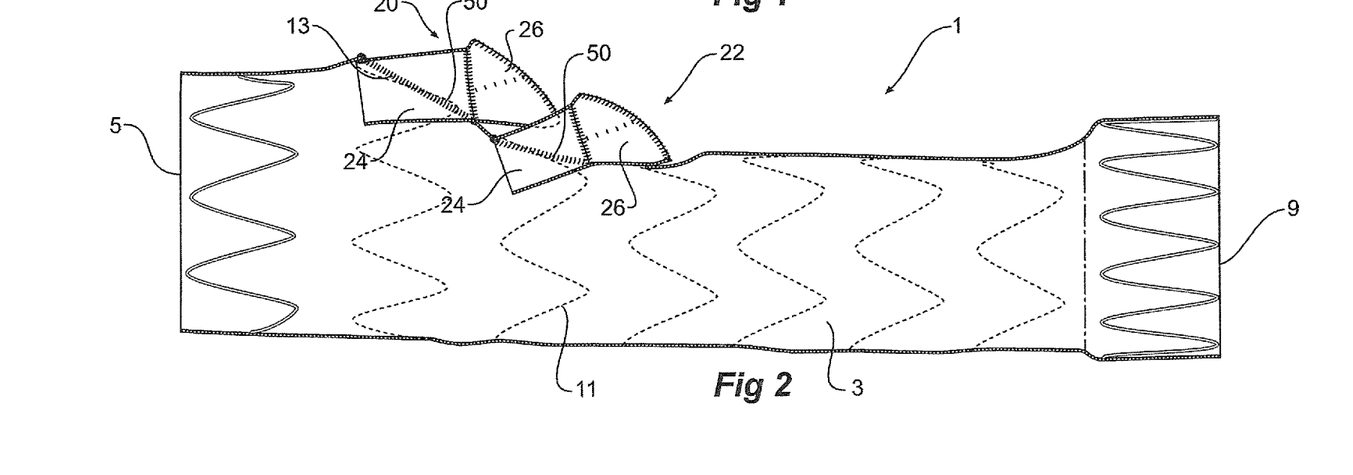
FIG. 2 shows the embodiment of FIG. 1 in longitudinal cross section.

FIG. 8 shows a schematic view of a portion of the human aorta showing how the stent graft as depicted in FIG. 1 can be deployed into the aorta.

The thoracic arch shown schematically comprises an ascending aorta 60 extending to the thoracic arch 62 and a descending aorta 64 from the thoracic arch. Substantially at the top of the thoracic arch but slightly to the ventral side of the arch the major vessels branch off the arch. The major vessels are the brachiocephalic artery 66, the common carotid artery 68 and the left subclavian 70. In a preparatory operation an anastomosis 74 is provided between the common or left carotid artery 68 and the left subclavian 70. The anastomosis provides access between the common carotid artery 68 and the left subclavian artery 70 which enables endovascular access to the stent graft via brachial arteries the left arm rather than endovascular access via the left carotid artery which may be more complex.

The stent graft 1 is deployed into the thoracic arch by known techniques. The proximal end 5 of the stent graft 1 extends down the ascending aorta 60. The distal end of the stent graft 9 extends down the descending aorta 64. The stent graft 1 is deployed in the thoracic arch 62 so that the angled end of the funnel portion 26*a* of the proximal combination guide and tubular side arm assembly 20 is adjacent or just proximal of the opening 66*a* of the brachiocephalic artery 66 into the thoracic arch and the funnel portion 26*a* encompasses the opening 66*a*. Similarly the angled end of the funnel portion 26*b* of the distal combination guide and tubular side arm assembly 22 is adjacent or just proximal of the opening 68a of the left carotid artery 68 into the thoracic arch and the funnel portion 26b encompasses the opening 68a. A flexible guide wire can then be extended as shown by the arrow 76 from the brachiocephalic artery 66 and would have a good chance of being received in the funnel portion 26a and be directed into the low profile side arm portion 24a thereby facilitating catheterization. Similarly a flexible guide wire extended as shown by the arrow 78 from the left subclavian artery 70 through the anastomosis 74 and into the left carotid artery 68 would have a good chance of being received in the funnel portion 26b and be directed into the low profile side arm portion 24b thereby facilitating catheterization.

When the stent graft of the present disclosure is deployed into the thoracic arch the circular ring portion 46 of the funnel frame 40 will tend to engage against the outer side of the curve of the thoracic arch and the guide assembly will hold the stent graft slightly away from the outer side of the curve and define a space into which a probe with a flexible tip can be inserted from a branch vessel and moved about until it enters the fenestration. Upon full deployment and with full blood pressure within the stent graft the lightweight space frame of the funnel portion will tend to collapse slightly and the stent graft can expand out to the vessel wall and provide less obstruction to blood flow. Hence by this disclosure there is provided a guide arrangement which facilitates catheterisation but does not cause continuing obstruction.

Throughout this specification various indications have been given as to the scope of this disclosure but the disclosure is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A thoracic arch stent graft assembly comprising
a tubular body of a biocompatible graft material, wherein the tubular body has a proximal end, a distal end, and a sidewall,
at least one aperture in the tubular body on one side thereof,
a sub-assembly of a guide and tubular side arm, the side arm having a longitudinal axis, and the sub-assembly mounted into the or each aperture, the sub-assembly comprising
a tubular portion and
a funnel portion extending from a distal end of the tubular portion, the funnel portion comprising a frusto-conical body comprising a smaller end and a larger end, the smaller end being connected to the tubular portion and the larger end comprising an angled open end oblique to the longitudinal axis of the tubular side arm,
the tubular portion and the funnel portion comprising a biocompatible graft material wall,
the tubular portion and the funnel portion both extend at least partially externally from the sidewall between the proximal end and the distal end of the tubular body, and
a lightweight space frame comprising a resilient wire, the lightweight space frame supporting the sub-assembly.

2. A thoracic arch stent graft assembly as in claim 1 wherein the space frame comprises a cylindrical portion and a funnel portion,
the cylindrical portion comprising first and second circular planar ring portions, the circular planar ring portions being parallel to each other and spaced apart axially, and at least two longitudinal struts extending between the first and second circular ring portions, and
the funnel portion comprising a funnel frame defined by a substantially circular ring portion to define a larger end of the funnel portion and a pair of spaced apart arms, the pair of spaced apart arms extending from the substantially circular ring portion towards the cylindrical portion.

3. A thoracic arch stent graft assembly as in claim 2 wherein the cylindrical portion comprises an assembly of a first ring and strut component and a second ring and strut component, each of the first and second ring and strut components comprising a circular planar ring portion and a strut extending at right angles to the circular planar ring portion from a periphery of the circular ring portion.

4. A thoracic arch stent graft assembly as in claim 3 wherein each of the first and second ring and strut components and the funnel frame comprise a single length of the resilient wire.

5. A thoracic arch stent graft assembly as in claim 1 comprising two apertures in the tubular body on one side thereof and the two apertures being spaced longitudinally apart and the sub-assembly of a guide and tubular side arm being mounted into each of the two apertures.

6. A thoracic arch stent graft assembly as in claim 1 comprising two apertures in the tubular body on one side thereof and the two apertures being spaced both longitudinally and circumferentially apart and the sub-assembly of a guide and tubular side arm being mounted into each of the two apertures.

7. A thoracic arch stent graft assembly as in claim 1 wherein the or each aperture is elliptical and the sub-assembly of a guide and tubular side arm is mounted into the elliptical aperture whereby a proximal end of the sub-assembly extends proximally within the tubular body and a distal end of the sub-assembly extends distally and exteriorly of the tubular body.

8. A thoracic arch stent graft assembly as in claim 1 wherein the or each aperture comprises a periphery and the tubular portion is mounted into the aperture by being stitched to the tubular body around the periphery of the aperture.

9. A thoracic arch stent graft assembly as in claim 8 wherein the stitching by which the tubular portion is mounted into the aperture extends circumferentially and diagonally from a proximal end of the tubular portion to the distal end of the tubular portion such that the tubular portion extends from the tubular body at an angle thereto with the funnel portion opening distally.

10. A thoracic arch stent graft assembly as in claim 8 wherein the tubular body comprises a tapered portion and the or each aperture is in the tapered portion of the tubular body and wherein the stitching by which the tubular portion is mounted into the aperture extends circumferentially and diagonally from a proximal end of the tubular portion to the distal end such that the tubular portion extends parallel to the tubular body as a whole with the funnel portion opening distally.

11. A thoracic arch stent graft assembly as in claim 1 wherein the tubular body is supported by self expanding stents.

12. A thoracic arch stent graft assembly as in claim 11 wherein the stents are formed from nitinol.

* * * * *